(12) United States Patent
Weidner et al.

(10) Patent No.: US 11,369,541 B2
(45) Date of Patent: Jun. 28, 2022

(54) DEVICE AND METHOD FOR SUPPLEMENTING MUSCLE STRENGTH

(71) Applicant: EXOIQ GMBH, Hamburg (DE)

(72) Inventors: Robert Weidner, Hamburg (DE); Jens Peter Wulfsberger, Hamburg (DE); Zhejun Yao, Hamburg (DE)

(73) Assignee: EXOIQ GMBH, Hamburg (DE)

( * ) Notice: Subject to any disclaimer, the term of this patent is extended or adjusted under 35 U.S.C. 154(b) by 438 days.

(21) Appl. No.: 16/465,065

(22) PCT Filed: Nov. 20, 2017

(86) PCT No.: PCT/DE2017/101006
§ 371 (c)(1),
(2) Date: May 29, 2019

(87) PCT Pub. No.: WO2018/099512
PCT Pub. Date: Jun. 7, 2018

(65) Prior Publication Data
US 2019/0282426 A1 Sep. 19, 2019

(30) Foreign Application Priority Data
Nov. 30, 2016 (DE) ...................... 10 2016 123 153.3

(51) Int. Cl.
*A61H 1/02* (2006.01)
*A61F 5/01* (2006.01)
*B25J 9/00* (2006.01)

(52) U.S. Cl.
CPC ........... *A61H 1/0288* (2013.01); *A61F 5/013* (2013.01); *A61H 1/0237* (2013.01);
(Continued)

(58) Field of Classification Search
CPC ................ A61H 1/0288; A61H 1/0237; A61H 2201/14; A61H 2201/1638;
(Continued)

(56) References Cited

U.S. PATENT DOCUMENTS

| | | |
|---|---|---|
| 3,358,678 A | 12/1967 | Kultsar |
| 3,467,421 A | 9/1969 | Bentley |

(Continued)

FOREIGN PATENT DOCUMENTS

| | | |
|---|---|---|
| CN | 101511310 A | 8/2009 |
| CN | 203829106 U | 9/2014 |

(Continued)

OTHER PUBLICATIONS

International Search Report and Written Opinion dated Apr. 24, 2018, issued in PCT Application No. PCT/DE2017/101006, filed Nov. 22, 2017.

(Continued)

*Primary Examiner* — Quang D Thanh
(74) *Attorney, Agent, or Firm* — Workman Nydegger

(57) ABSTRACT

A device for muscle strength support includes a flexible support structure configured to be worn on a body of a user during use of the device and an actuator unit configured to exert a tensile force on a first tension member of the flexible support structure to support the muscle strength during a movement of a first body part. The first tension member extends along a first path through a guide strap of the flexible support structure to the actuator unit, the guide strap limiting a section of the first path in a direction perpendicular to a path longitudinal direction. The first tension member is further configured to be attached to the first body part during use of the device by a first fastening member.

15 Claims, 4 Drawing Sheets

(52) U.S. Cl.
CPC ......... *B25J 9/0006* (2013.01); *A61H 2201/14* (2013.01); *A61H 2201/165* (2013.01); *A61H 2201/1638* (2013.01); *A61H 2201/1642* (2013.01); *A61H 2201/5061* (2013.01); *A61H 2230/065* (2013.01); *A61H 2230/605* (2013.01)

(58) Field of Classification Search
CPC ...... A61H 2201/1642; A61H 2201/165; A61H 2201/5061; A61H 2230/065; A61H 2230/605; A61F 5/013; A61F 5/042; A61F 2005/0155; A61F 2005/0179; B25J 9/0006; A61B 5/11
See application file for complete search history.

(56) References Cited

U.S. PATENT DOCUMENTS

| | | | |
|---|---|---|---|
| 5,282,460 A | 2/1994 | Boldt | |
| 5,865,770 A | 2/1999 | Schectman | |
| 6,113,642 A | 9/2000 | Petrofsky et al. | |
| 2003/0004473 A1 | 1/2003 | Bonadio et al. | |
| 2003/0223844 A1 | 12/2003 | Schiele et al. | |
| 2006/0094989 A1* | 5/2006 | Scott | A61F 2/586 601/5 |
| 2007/0258671 A1 | 11/2007 | Siemer et al. | |
| 2008/0009771 A1 | 1/2008 | Perry et al. | |
| 2008/0188907 A1 | 8/2008 | Aguirre-Ollinger et al. | |
| 2010/0041521 A1 | 2/2010 | Ingvast et al. | |
| 2011/0004322 A1 | 1/2011 | Sankai | |
| 2012/0022666 A1* | 1/2012 | Brooks | A61F 2/586 623/24 |
| 2012/0172770 A1 | 7/2012 | Almesfer et al. | |
| 2014/0212243 A1 | 7/2014 | Yagi et al. | |
| 2014/0243721 A1* | 8/2014 | Bryant | A61F 5/013 602/21 |
| 2015/0266181 A1 | 9/2015 | Kornbluh et al. | |
| 2015/0366694 A1 | 12/2015 | Bujold et al. | |
| 2016/0058647 A1 | 3/2016 | Maddry | |
| 2016/0067061 A1 | 3/2016 | Nagarajan et al. | |
| 2016/0325428 A1 | 11/2016 | Chun | |
| 2017/0259427 A1 | 9/2017 | Asada et al. | |
| 2018/0296419 A1* | 10/2018 | Tong | A61H 1/02 |

FOREIGN PATENT DOCUMENTS

| | | | |
|---|---|---|---|
| CN | 104552276 A | 4/2015 | |
| CN | 104552276 B | 2/2016 | |
| CN | 105415353 A | 3/2016 | |
| CN | 106313012 A | 1/2017 | |
| CN | 106335049 A | 1/2017 | |
| CN | 106945017 A | 7/2017 | |
| CN | 206588942 U | 10/2017 | |
| CN | 105415353 B | 1/2018 | |
| CN | 106313012 B | 5/2018 | |
| CN | 106335049 B | 8/2018 | |
| DE | 307250 C1 | 9/1917 | |
| DE | 102011076843 A1 | 12/2012 | |
| DE | 102011076843 B4 | 5/2014 | |
| EP | 1364755 A1 | 11/2003 | |
| EP | 1364755 B1 | 11/2009 | |
| EP | 2796114 A1 | 10/2014 | |
| EP | 2796114 B1 | 3/2016 | |
| EP | 3189945 A1 | 7/2017 | |
| EP | 3189945 B1 | 9/2018 | |
| ES | 2544890 A1 | 9/2015 | |
| FR | 779284 A | 4/1935 | |
| FR | 2993811 A1 | 7/2012 | |
| FR | 3046110 A1 | 12/2015 | |
| JP | 03-665879 B2 | 4/2005 | |
| JP | 2012024557 A | 2/2012 | |
| JP | 2012239818 A | 12/2012 | |
| KR | 10-2012-065470 A | 6/2012 | |
| WO | 2005/105004 A1 | 11/2005 | |
| WO | 2010/019300 A1 | 2/2010 | |
| WO | 2010/019300 A9 | 2/2010 | |
| WO | 2010/080774 A2 | 7/2010 | |
| WO | 2011/127421 A1 | 10/2011 | |
| WO | 2012/099995 A2 | 7/2012 | |
| WO | 2012/099995 A3 | 8/2012 | |
| WO | 2014/093408 A2 | 6/2014 | |
| WO | 2014/093408 A3 | 9/2014 | |
| WO | 2014/195373 A1 | 12/2014 | |
| WO | 2015/078981 A1 | 6/2015 | |
| WO | 2015/157473 A2 | 10/2015 | |
| WO | 2016/012480 A1 | 1/2016 | |
| WO | 2016/015070 A1 | 2/2016 | |
| WO | 2016/146960 A1 | 9/2016 | |
| WO | 2016/174091 A1 | 11/2016 | |
| WO | 2016/187275 A1 | 11/2016 | |
| WO | 2017/109190 A1 | 6/2017 | |
| WO | 2017/109193 A1 | 6/2017 | |
| WO | 2017/109196 A1 | 6/2017 | |
| WO | 2017/109197 A1 | 6/2017 | |
| WO | 2017/109202 A1 | 6/2017 | |
| WO | 2017/167349 A1 | 10/2017 | |

OTHER PUBLICATIONS

Chinese First Office Action and Search Report, English Translation, dated Oct. 30, 2018, for Chinese Application No. 201780074285.5 filed Nov. 22, 2017.

* cited by examiner

DEVICE AND METHOD FOR SUPPLEMENTING MUSCLE STRENGTH

TECHNICAL FIELD

The present invention relates to devices and methods for supporting muscular strength. In particular, the invention relates to a device and a method for supporting the hand muscles.

BACKGROUND

Manual activities, especially those based on repetitive and intense hand movements, can lead to diseases of the human musculoskeletal system. This can result in reduced muscle strength and connective tissue problems. For instance, affected persons may lose the ability to apply a sufficient gripping or rather a sufficient finger force, which may lead to problems when holding and manipulating objects, or affected persons may be impaired in their mobility due to persistent overload pain or symptoms of wear and tear.

In addition to said diseases of the human musculoskeletal system, a muscular strength that is reduced or (in a given situation) too low may also be due to the use of hindering (protective) gloves, poor accessibility, or the need to hold or manipulate heavy or stiff objects.

To support muscle strength or to rehabilitate diseases of the hand, various portable devices are known from the prior art. U.S. Pat. No. 3,707,963 A, EP 2436358 A1, WO 2014/033613 A2 and WO 2014/068509 A2, for example, show self-supporting devices constructed from rigid elements, by which movements of a hand can be guided and supported. Devices of this type must ideally be designed in a way that their pivot points coincide with the axes of rotation of the human joints. Otherwise, deviations can lead to disorders and injuries of the user as well as to restrictions of the human movements. To meet this requirement, a rigid structure requires additional space, which is often difficult to come by in the hand area.

Furthermore, U.S. Pat. No. 7,573,577 B2 discloses a flexible orthopedic glove which has spring elements on the dorsal side of the hand that support extending the fingers. In addition, the glove can be used for training the grip force. U.S. Pat. Nos. 8,029,414 B2 and 9,067,325 B2 in turn show gloves that are equipped or coupled with tension members and motors for grip intensification, particularly for the power-grip. These devices thus focus mainly on supporting the power grip, in particular the variant of the power grip in which all fingers and the thumb surround the object. However, to the best of the inventors' knowledge, a device that can support the variety of all possible grips and hand movements is not known in the art.

DISCLOSURE OF INVENTION

It is the object of the present invention to improve the concepts for supporting human movements that are known from the prior art.

To this end, the present invention provides a biomimetic device according to claim 1 which replicates the function of the muscles and the connective tissue interacting with the muscles of a human body part (in particular a hand), in the form of a wearable (textile) garment.

The muscle strength support device according to the invention comprises a flexible support structure which is configured to be worn on a body of a user during use of the device and an actuator unit which is configured to exert a tensile force on a first tension member of the flexible support structure to support the muscle strength during a movement of a first body part, wherein the first tension member extends along a first path through a guide strap of the flexible support structure to the actuator unit, the guide strap limiting a section of the first path in a direction perpendicular to a path longitudinal direction, the first tension member is configured to be attached to the first body part during use of the device by a first fastening member, and the guide strap is positioned along the force transmission direction past the first fastening member.

The flexible support structure may be configured to be put over a limb, in particular over one or more fingers of a user's hand.

The actuator unit may be configured to be attached to the user by a bandage or an arm or leg strap.

The flexible support structure may comprise a plurality of tension members fastened in particular on a palmar side and a dorsal side of the support structure, wherein the tension members are guided along different paths in the support structure to the actuator unit and the actuator unit is adapted to exert tensile forces on the tension members.

The flexible support structure may at least be partially provided with a polymer layer on the inside and/or the outside.

For instance, the flexible support structure may comprise an outer layer (e.g. a polymer layer) covering the tension members.

Here, the term "flexible support structure", as used throughout the description and the claims, is to be understood, in particular, as a structure that includes flexible elements, e.g. textile elements, which may transmit force on a body part such as a limb, or on sections or parts of a limb. Due to the flexibility of the support structure, the force is, in particular, not substantially punctually applied, but (evenly) distributed over a specific area of the body part. Furthermore, the flexibility of the support structure allows the user to influence the force direction within certain limits or to deviate from a given force direction within certain limits, which allows for a more natural movement.

Furthermore, the term "actuator unit", as used throughout the description and the claims, is to be understood, in particular, as a unit which is configured, under the control of electrical signals, to apply a force to members which are connected to the actuator unit. Because the actuator unit can be attached to the user during use of the device by means of a bandage or an arm or leg strap, the tension members can hence be moved relative to the bandage or relative to the arm or leg strap. Due to the relative movement, a movement of the limb or parts of the limb can be initiated or supported.

Furthermore, the term "bandage", as used throughout the description, is to be understood, in particular, as an expandable element that (during use of the device) is force-fittedly slung around an arm, a leg, or another body part, wherein, for instance, the expandable element may take the form of a strap (i.e., an arm strap, a leg strap, or a strap or belt around a body part). The bandage may for example be made of an elastic material, which is wound around the arm or the leg during use of the device in an expanded state and is force-fittedly connected to the arm or the leg due to the restoring force of the elastic material.

Furthermore, the wording "palmar/dorsal side of the support structure", as used throughout the description, is to be understood, in particular, as a portion of the support structure which is adjacent or opposite to the palmar/dorsal side of the hand. In addition, the term "tension member", as used throughout the description and the claims, is to be understood, in particular, as an element (for example a wire, a thread, a string, a cable, a ribbon, or a rubber ribbon) which is adapted to transmit a force exerted by the actuator unit to a connection point. In this context, the term "path", as used throughout the description and the claims, is to be understood, in particular, as a (straight or curved) trajectory along which a corresponding tension member can be (slidingly) displaced during use of the device. Here, the term "trajectory" shall be construed broadly and also include defined deviations perpendicular to the direction of motion from an "ideal line", which may occur, for example, in case of a guide with play and/or a guide that is made of an elastic material.

In addition, it should be noted that adjectives such as "first, second, third, etc.", as used throughout the description and the claims, primarily serve to differentiate between terms, or elements that are referred to by said terms. For example, a reference to a "third tension member" does not mean that the invention requires a first and a second tension member, but merely serves to simplify the reference to a particular tension member in regard to embodiments that include more than one tension member. Furthermore, adjectives such as "first, second, third, etc.", as used throughout the description and the claims, should not be construed as necessarily referring to different features, because embodiments may exist in which different functions can be effected by different (identical) features or by a single feature.

Preferably, the flexible support structure is formed as a glove, wherein the one or more fingers of the user's hand are enclosed by one or more sheaths of the glove.

Here, the term "glove", as used throughout the description and the claims, is to be understood, in particular, as a textile garment, which encloses the one or more fingers of the user's hand, the metacarpus, and often also the carpus, wherein the term "enclosed" is to be construed broadly and shall include gloves with one or more openings, for instance for ventilation. Moreover, in addition to an elastic glove which (in the expanded state) force-fittingly encloses the one or more fingers and the carpus of the hand during use, a glove is envisaged which force-fittingly encloses during use, in the expanded state, only certain portions of the one or more fingers and the carpus.

Preferably, each tension member is secured to a ribbon-shaped loop of the flexible support structure, wherein at least one loop of the flexible support structure is configured to loop around a finger bone of the hand, and at least one loop of the flexible support structure is adapted to loop around metacarpal bones of the hand.

By exercising a tensile force on a tension member by the actuator unit, the loop connected to the tension member can be pulled in the direction of the path or in the direction of a path section, towards the actuator unit. As a result, the finger bone with the loop around it is flexed if the path extends along the palmar side and extended if the path extends along the dorsal side of the hand, or the carpus with the loop around it becomes more strongly arched.

Preferably, the number of loops of the flexible support structure that are configured to loop around a single finger is greater than or equal to the number of finger bones (phalanges) of said single finger.

This allows addressing each finger bone individually and thus allows supporting complex hand movements. For instance, at least one loop may be provided per finger bone of a finger, wherein, during use of the device, the loop loops around said finger bone at its distal end or within a region at the distal end.

The at least one loop of the flexible support structure which is configured to loop around the metacarpal bones of the hand is, preferably, further configured to extend along a muscle ridge on the palm side of a metacarpus, at the thumb and at the little finger.

Thus, the enclosed metacarpus may, for example, be supported in regard to the power grip, by guiding the metacarpal bone of the thumb towards the palm.

Preferably, the tension members are guided through loops of the flexible support structure.

This enables a flat guide that is close to the body, which achieves a defined movement of the individual phalanges relative to each other.

Preferably, the actuator unit comprises a plurality of tension units, which comprise, in particular, elements which are made of a shape memory alloy.

In this regard, the term "shape memory alloy", as used throughout the description and the claims is to be understood, in particular, as an alloy which, in the solid state, transitions into a particular shape when changing physical parameters (e.g. by heating) and can thus be used to perform work.

The elements made of a shape memory alloy are preferably helical.

By using spring-like elements made of a shape memory alloy, it is possible to realize an elastic connection of the tension members to the actuator unit and keep the actuator unit compact.

Preferably, the flexible support structure comprises an arm portion configured to be put over a forearm of the user, and a pulling direction of the actuator unit extends along the forearm.

This allows that the actuator unit can be attached in a flexible and adaptive way, which prevents hand movements from being obstructed by the actuator unit or prevents that the hand-surrounding part of the device obstructs or inhibits the access to or the manipulation of objects that are difficult to access.

Preferably, the first path is configured to pass over a joint of the body which connects a bone of the first body part to a bone of a second body part.

This allows supporting, by the tensile force, flection, extension, abduction, adduction, or rotation of the joint.

Preferably, the first path is configured to extend, at least in sections, in parallel to a tendon and/or a muscle of the body which allow applying a voluntary muscular force to the first body part.

This allows for muscle strength support which is adapted to natural movements.

The first tension member preferably has a first fastening member (for example a loop) which is configured to completely or partially surround the first body part during use of the device.

This reduces the dependence of the force transmission on the position of the first body part.

Preferably, the device further comprises a second tension member which is guided along a second path to the actuator unit and is configured to be attached to the first body part, during use of the device, by the first fastening member.

This expands the possibilities with regard to the supported movement direction(s) in regard to the first body part.

Preferably, the actuator unit is configured to exert mutually independent tensile forces on the first tension member and the second tension member.

As a result, antagonistic movements of the first body part can be supported.

Preferably, the device further comprises a third tension member which is guided along a third path to the actuator unit and is configured to be attached to a third body part during use of the device, wherein a third fastening member of the third tension member is formed as the guide strap.

This allows reducing the complexity of the support structure.

Preferably, the guide strap is configured to enclose a/the second body part.

The guide strap and the fastening member(s) may, for example, be made of a flexible material or a combination of materials, which are flexible in a direction perpendicular to the tensile direction, but substantially inelastic in the pulling direction in view of the expected tensile forces.

Preferably, the flexible support structure is configured to be worn on the skin or over a garment during use of the device and is provided with a polymer layer.

For instance, the guide strap can be provided with a slip-resistant silicone layer.

Preferably, the first fastening member is configured to be worn on the skin or over a garment, during use of the device, and is provided with a polymer layer.

For instance, the fastening member can be provided with a slip-resistant silicone layer.

Preferably, the guide strap has a channel and the first tension member passes through the channel.

As a result, a contact between the tension member and the skin can be avoided.

Preferably, the device further comprises a control system with a sensor unit, wherein the control system is configured to control the first tensile force.

Preferably, the sensor unit comprises sensors for detecting a force, a movement, a stretch, a flection, a muscle activity, a pulse rate, and/or a metabolic rate.

Preferably, the control system is configured to minimize the energy costs of the user while using the device.

Preferably, the actuator unit comprises a shape memory alloy spiral shaped element to which the first tension member is attached.

However, the actuator unit may also comprise an electric motor, a pneumatic or hydraulic actuator, or artificial muscles made of polymer fibers or carbon nanotubes.

Preferably, the flexible support structure is formed at least as a part of a textile garment.

For instance, the flexible support structure may comprise a sleeve, a vest, pants, a trouser leg, a stocking, or a sock. Furthermore, the guide strap and/or the fastening members may be incorporated into the textile garment.

Preferably, the device is attached to a person's body, voluntary movements of the hand are monitored, and tensile forces are exerted on the tension members based on the monitored voluntary movements.

This allows supporting a variety of hand movements of a person.

BRIEF DESCRIPTION OF DRAWINGS

The invention will be explained in more detail in the following detailed description on the basis of exemplary embodiments, wherein reference is made to the drawings in which.

In the drawings, the same and functionally similar elements are designated by the same reference numerals.

MODE(S) FOR CARRYING OUT THE INVENTION

Figure 1:
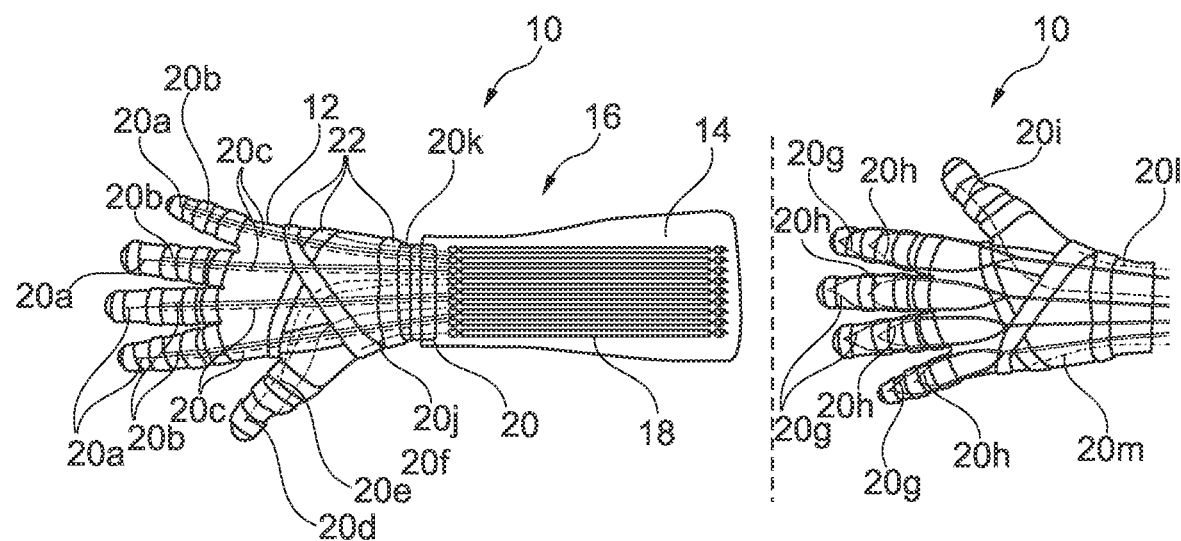
FIG. 1 shows a schematic view of an exemplary embodiment of a device according to the invention.
Figure 2:
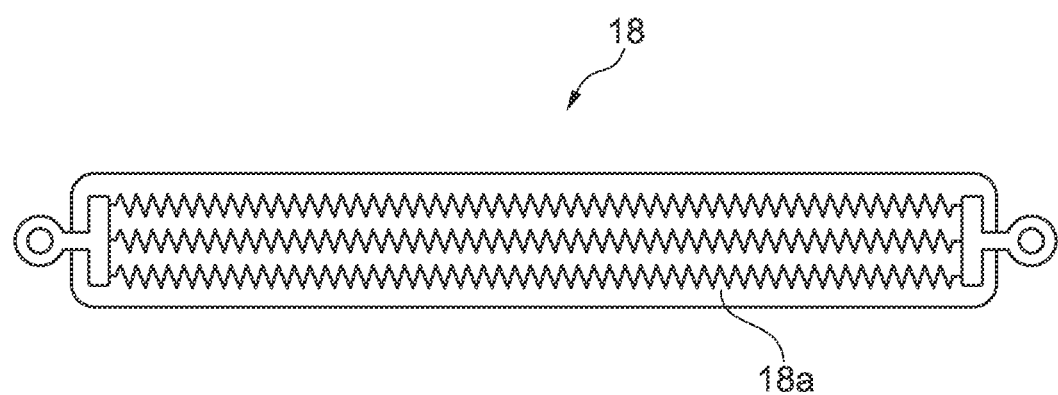
FIG. 2 shows a schematic view of an exemplary embodiment of a tensile member.

FIG. 1 shows a schematic view of the palmar side (left) and a schematic view of the dorsal side (right) of a device 10 for muscle strength support. The device 10 comprises a flexible support structure 12 in the form of a finger glove and a forearm bandage 14 which is connected to the support structure 12. Attached to the forearm bandage 14 is an actuator unit 16 with a plurality of tension units 18. As shown in FIG. 2, the tension units 18 may each comprise a plurality of helical elements 18a made of a shape memory alloy, the length of which can be shortened by means of a control signal of a controller (not shown). It should be noted, however, that in regard to the tension units 18, the invention is not limited to helical elements 18a made of a memory alloy; rather, the required tensile forces may be generated by arbitrary artificial muscles (for example, by artificial muscles made of twisted plastic fibers or carbon nanotubes) or by electric motors.

As shown in FIG. 1, the tensile units 18 are connected at their proximal end to the forearm bandage 14 and at their distal end to a plurality of tension members 20, which are depicted along their paths partly by solid lines and partly by dashed lines (for the sake of clarity). The tension members 20 are formed as wires or (monofilament) strings, the distal end of each being attached to a fastening member which is formed as a ribbon-shaped loop 22. The ribbon-shaped loops 22 are integrated/incorporated into the finger glove, so that slippage of the loops 22 in the distal or proximal direction is (substantially) prevented. By displacing the tension members 20, the loops 22 tighten around the finger bones and exert a force on the finger bones. In this regard, it should be noted that the force is exerted on the finger bones by the portions of the loops 22 opposite to the tension members 20.

To this end, the loops 22 are preferably flexible perpendicular to the pulling direction but nevertheless (substantially) not extendable. Thus, the loops 22 that tighten around the finger bones adapt to the shape of the user's finger without impairing the transmission of the tensile forces. Furthermore, as shown in FIG. 1, one pulling member 20 on a palmar side and another one on a dorsal side of a hand may be connected pairwise, and offset relative to each other, with a loop 22, so that it is possible to support a movement in different directions and in particular to support flexing and extending of the hand bones.

As shown in FIG. 1, the paths of the tension members 20a, 20b and 20c on the palmar side extend along the midlines of the index finger, the middle finger, the ring finger, and the little finger, and are adapted for flexing the respective finger. The paths of the tension members 20a are derived from the paths of the tendons of the M. flexor digitorum profundus (FDP) and are directed at directly supporting the flection of the distal phalanges and indirectly supporting the flection of the intermedial phalanges and the proximal phalanges. The paths of the tension members 20b are derived from the paths of the tendons of the M. flexor digitorum superficialis (FDS) and are directed at directly supporting the flection of the intermedial phalanges and indirectly supporting the flection of the proximal phalanges. The paths of the tension members 2c are derived from the paths of the tendons of the Mm. Interossei (IOs) and are directed at supporting the flection of the proximal phalanges.

The flection and opposition of the thumb can be supported by the tension members 20d and 20e while the tension member 20f supports abducting the thumb. Whereas the paths of the tension members 20a-20c extend along the midline of the fingers, the paths of the tension members 20d-20f do not extend along the midline of the thumb but offset from the midline along the palm of the hand to the wrist. This path improves the power flow as regards the tension elements 20d-20f and allows a precise force-supporting guidance of the metacarpal bone of the thumb.

The extension of the phalanges of the index finger, the middle finger, the ring finger, and the little finger can be supported by the tension members 20g and 20h. As shown in FIG. 1, the tension members 20g and 20h split at the level of the distal ends of the metacarpal bones, respectively, into two strands which are offset from the midline of the phalanges. This improves the wearing comfort. Further, the tension member 20i supports the extension and positioning of the thumb at rest.

The tension members 20j, 20k, 20l, and 20m are directed at the movements of the wrist and configured to be actuated, i.e., loaded with a force or tensioned, independently of the tension members 20a-20i, which act directly on the phalanges. The tension members 20j and 20k support the flection of the palm, whereas the tension members 20l and 20m support the extension of the palm. The abduction and adduction of the palm can be supported by the tension members 20j and 20l and by the tension members 20k and 20m, respectively. By a coordinated loading of the tension members 20j-20l with force, the alignment of the wrist can also be supported.

Figure 3:
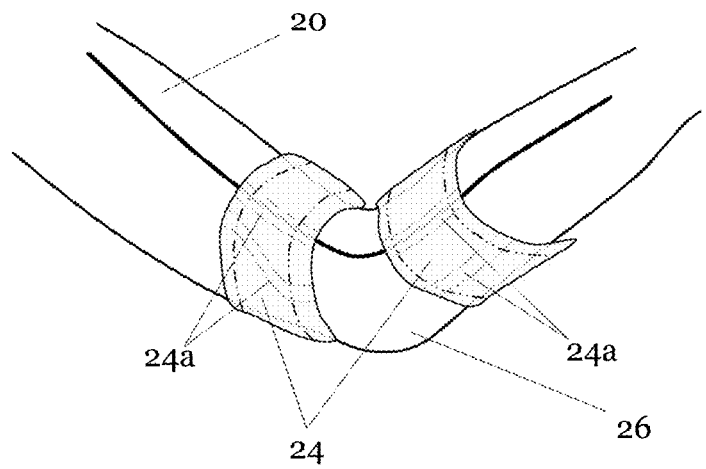
FIG. 3 shows a schematic view of an exemplary embodiment of a portion of the flexible support structure.

FIG. 3 shows an exemplary embodiment of a guide of a tension member 20 along an inner side of the flexible support structure 12. The ribbon-shaped guide straps 24 are provided with guide elements in the form of channels 24a, through which the tension elements 20 extend. Alternatively, the tension element 20 may also be guided between the upper arm and the forearm, respectively, and the guide strap 24 through the guide strap 24. The channels 24a delimit the path of the tension members 20 transversely to the direction of displacement and thereby form a guide which slidingly guides the tension members 20 along defined paths. As shown in FIG. 3, curved channels 24a may be provided in addition to or instead of rectilinear channels 24a. Furthermore, to protect the human skin, a continuous (textile) protective layer may be provided between the tension members 20 and the skin surface, such that a direct contact between the tension members 20 and the skin is avoided.

Moreover, as shown in FIG. 1, loops 22 serving as guide straps 24 may not only be provided at the distal ends of the phalanges for flexing the fingers, but also at the proximal ends of the phalanges, for instance, at the proximal ends of the proximal phalanges, to provide for a defined guidance of the tension members 20 that is close to the body even when the phalanges are flexed.

Figure 4:
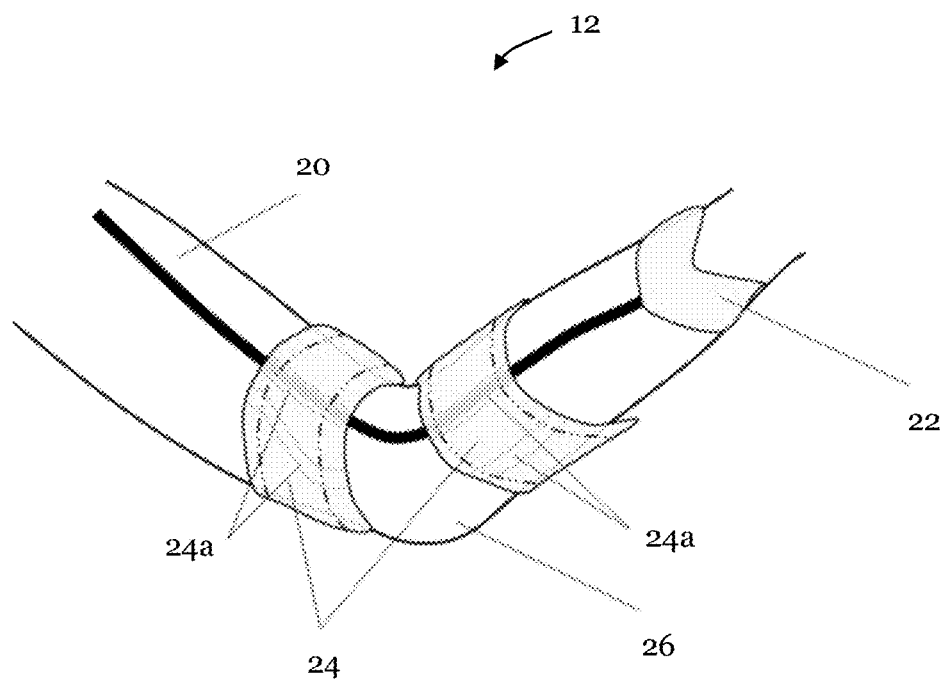
FIG. 4 shows a schematic view of an exemplary embodiment of a flexible support structure of another device according to the invention.

FIG. 4 shows a schematic view of an exemplary embodiment of a flexible support structure 12 of a further device 10 according to the invention for supporting the movement (in particular the flection) of a forearm of the user. As shown in FIG. 4, the flexible support structure 12 comprises a tension member 20 with a fastening element in the form of a loop 22 surrounding a user's forearm. The tension element 20 is guided through channels 24a of the guide straps 24 surrounding the forearm and upper arm, which effect a close-to-the-body guidance of the tension member 20 even when the forearm is bent. Alternatively, the tension element 20 may also be guided between the upper arm and the forearm, respectively, and the guide strap 24 through the guide strap 24.

Figure 5:
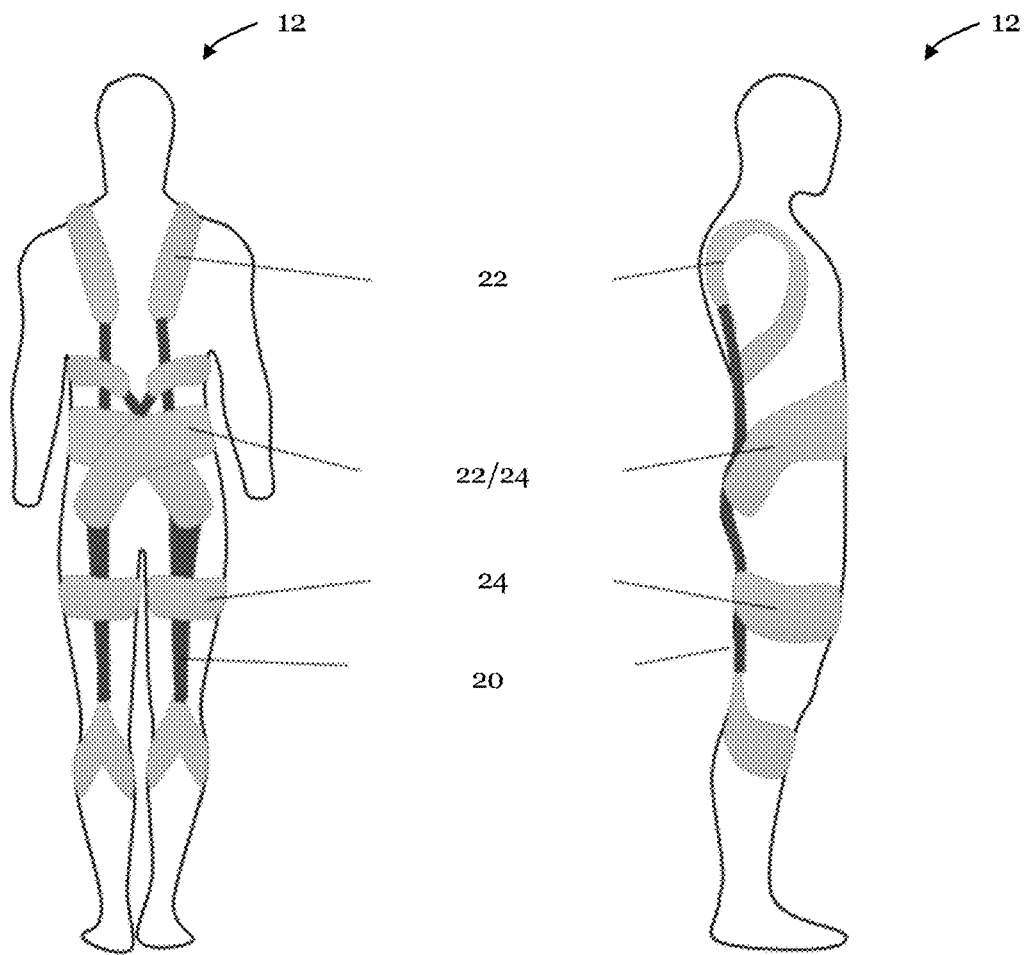
FIG. 5 shows schematic views of an exemplary embodiment of a flexible support structure of yet another device according to the invention.

FIG. 5 shows a schematic view of an exemplary embodiment of a flexible support structure 12 of a further device 10 according to the invention for supporting the movement of the legs and the trunk of the user. As shown in FIG. 5, the flexible support structure 12 comprises tension members 20 which comprise fastening elements in the form of loops 22 surrounding a user's lower legs. The tension elements 20 are guided through guide straps 24 surrounding the thighs, which effect a close-to-the-body guidance of the tension members 24 even when the lower legs are flexed. Further, the flexible support structure 12 comprises tension members 20 which enclose the upper body and the lower body of the user and by which the extending of the spine can be supported.

Figure 6:
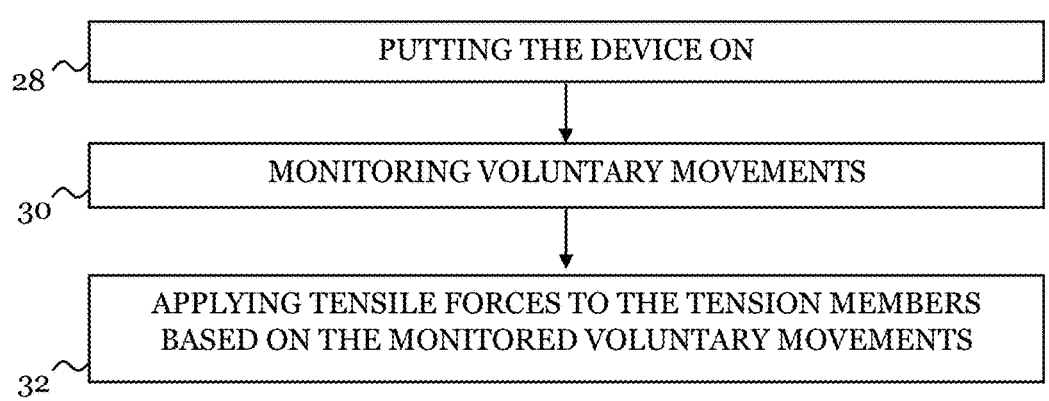
FIG. 6 shows a method for muscle strength support.

FIG. 6 outlines the use of the device 10 in a muscle strength support method. After putting 28 the device 10 on, voluntary movements of a body part, such as, for example, the hand, are monitored by electromyographic (EMG) sensors or force sensors 30. If a voluntary movement is detected or a detected force value exceeds a predetermined threshold, tensile forces may be exerted 32 on some of the tension members 20 to support the musculature, i.e., to reduce the force to be provided by the muscular system in a given situation by providing it through the device 10.

Figure 7:
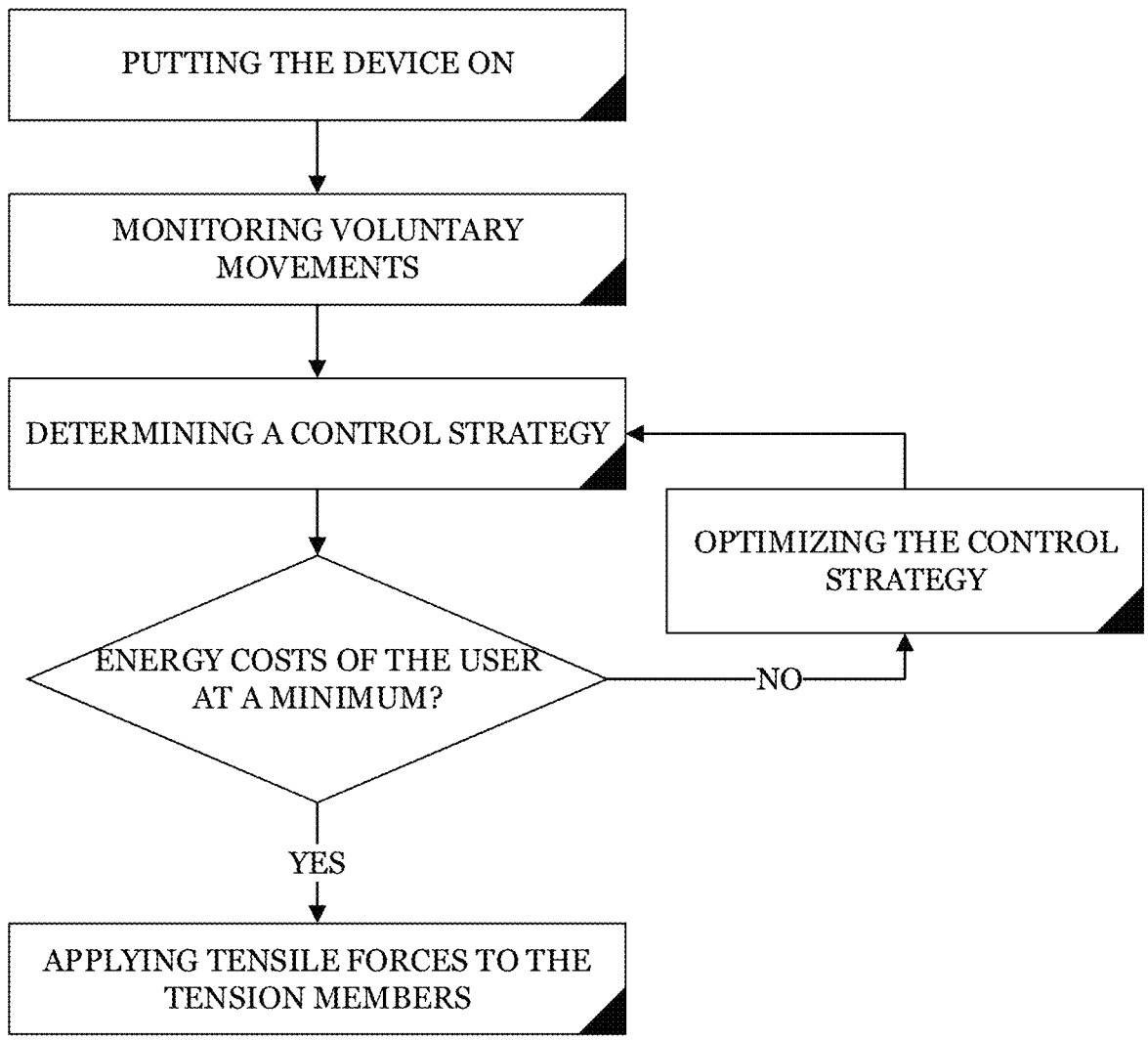
FIG. 7 shows another method for muscle strength support.

FIG. 7 outlines the use of the device 10 in another muscle strength support method. After putting the device 10 on, voluntary movements of a body part, such as, for example, the hand, are monitored by electromyographic (EMG) sensors or force sensors. If a voluntary movement is detected or a detected force value exceeds a predetermined threshold, tensile forces may be exerted on some of the tension members 20 to support the musculature, i.e., to reduce the force to be provided by the muscular system in a given situation by providing it through the device 10. The tensile forces to be applied by the device 10 to a part of the tension members 20 are determined on the basis of a control strategy which is optimized until the energy costs of the user, i.e., the sum of the energy to be provided by the user over a certain time horizon, are minimal.

The shown device 10 is thus designed as a portable support system that supports or relieves corresponding muscles of the user. In this context it should be noted, however, that the shown device 10 (modified according to the changing anatomical conditions) can be used for supporting all body parts, such as the arms, the legs, the feet, or even the back, in that the function of the human muscles and the cooperating connective tissue is adequately replicated by the device 10.

The replication, by the device 10, of the function of the human muscles as well as the connective tissue cooperating therewith is, as described exemplary in connection with FIG. 1-7, achieved by the cooperation of the actuator unit 16, the tension members 20 and the guide straps 24. The actuator unit 16 may be directly or indirectly connected to the tension members 20 and designed in a way that the tension members 20 and the actuator unit 16 can be independently added to the flexible support structure 12 or rather independently attached to the forearm sleeve 14, while putting 28 the device 10 on.

The invention claimed is:

1. A muscle strength support device comprising:
   a flexible support structure configured to be worn on a body of a user during use of the device, the flexible support comprising:
     a glove having one or more sheaths configured to surround one or more fingers of the user's hand, the glove having a palm side and an opposing dorsal side;
     a first fastening member secured to a select one of the one or more sheaths of the glove so that when a phalange is received within the select sheath, the first fastening member at least partially encircles the phalange;
     a first guide strap secured to the select sheath proximal of the first fastening member;
     a first tension member positioned on the palm side of the glove and extending along the select sheath so that when the phalange is received within the select sheath, the first tension member extends along a midline of the phalange on the palm side, the first tension member passing through the first guide strap and having a distal end connected to the first fastening member, the first guide strap limiting lateral movement of the first tension member; and
     a second tension member positioned on the dorsal side of the glove and having a distal end connected to the first fastening member, the second tension member splitting into two strands proximal of the first fastening member so that when the phalange is received within the select sheath, the two strands extend along separate paths that are spaced apart from and are adapted to be disposed on opposite sides of the midline of the phalange on the dorsal side; and
   an actuator unit configured to exert a tensile force on the first tension member of the flexible support structure to support a muscle strength of the user during a movement of a first body part of the user; wherein
   the first tension member extends along a first path through theft first guide strap of the flexible support structure to the actuator unit.

2. The muscle strength support device of claim 1, wherein the first tension member is configured to pass over a joint of the body, the joint connects a bone of the first body part to a bone of a second body part.

3. The muscle strength support device of claim 2, further comprising:
   a third tension member guided along a third path to the actuator unit and configured to be attached to a third body part during use of the device, wherein a third fastening member of the third tension member is formed as the first guide strap.

4. The muscle strength support device of claim 1, wherein the first tension member is configured to run, at least in sections, parallel to a tendon and/or a muscle of the body, the tendon and/or muscle allows applying a voluntary muscular force to the first body part.

5. The muscle strength support device of claim 1, wherein the second tension member is guided along a second path to the actuator unit and configured to be attached to the first body part during use of the device by the first fastening member.

6. The muscle strength support device of claim 5, wherein the actuator unit is configured to exert mutually independent tensile forces on the first tension member and the second tension member.

7. The muscle strength support device of claim 1, wherein the first guide strap is configured to enclose a second body part.

8. The muscle strength support device of claim 1, wherein the first guide strap has a channel and the first tension member passes through the channel.

9. The muscle strength support device of claim 1, further comprising:
   a control system with a sensor unit, wherein the control system is configured to control the tensile force produced by the actuator unit; and
   the control system is configured to minimize an energy costs of the user while using the device.

10. The muscle strength support device of claim 9, wherein the sensor unit comprises sensors for detecting a force, a movement, a stretch, a flection, a muscle activity, a pulse rate, and/or a metabolic rate.

11. The muscle strength support device of claim 1, wherein the actuator unit comprises a helical element made of a shape memory alloy, the first tension member being attached to the helical element.

12. The muscle strength support device of claim 1, wherein the flexible support structure is at least partially provided with a polymer layer on an inside and/or an outside.

13. The muscle strength support device of claim 1, wherein the flexible support structure further comprises an arm portion configured to be put over a forearm of the user, the actuator unit having a pulling direction that extends along the forearm.

14. A method for muscle strength support, comprising:
    putting on the device according to claim 1;
    monitoring voluntary movements; and
    applying the tensile force to the first tension member based on the monitored voluntary movements.

15. A muscle strength support device comprising:
    a flexible support structure configured to be worn on a body of a user during use of the device, the flexible support comprising:
      a glove having one or more sheaths configured to surround one or more fingers of the user's hand, the glove having a palm side and an opposing dorsal side;
      a first fastening member secured to a select one of the one or more sheaths of the glove so that when a phalange is received within the select sheath, the first fastening member at least partially encircles the phalange;
      a first tension member positioned on the palm side of the glove and extending along the select sheath so that when the phalange is received within the select sheath, the first tension member extends along the phalange on the palm side, the first tension member having a distal end connected to the first fastening member; and
      a second tension member positioned on the dorsal side of the glove and having a distal end connected to the first fastening member, the second tension member splitting into two strands proximal of the first fastening member so that when the phalange is received within the select sheath, the two strands extend along separate paths that are spaced apart from and are disposed on opposite sides of the midline of the phalange on the dorsal side; and an actuator unit configured to exert a tensile force on the first tension member of the flexible support structure to support a muscle strength of the user during a movement of a first body part of the user.

* * * * *

UNITED STATES PATENT AND TRADEMARK OFFICE
CERTIFICATE OF CORRECTION

PATENT NO. : 11,369,541 B2
APPLICATION NO. : 16/465065
DATED : June 28, 2022
INVENTOR(S) : Robert Weidner et al.

It is certified that error appears in the above-identified patent and that said Letters Patent is hereby corrected as shown below:

On the Title Page

Item (22), PCT Filed, change "Nov. 20, 2017" to – Nov. 22, 2017 –

Signed and Sealed this
Third Day of January, 2023

Katherine Kelly Vidal
*Director of the United States Patent and Trademark Office*